(12) United States Patent
Lian et al.

(10) Patent No.: US 8,788,026 B2
(45) Date of Patent: Jul. 22, 2014

(54) METHODS AND DEVICES FOR DETERMINATION OF HEART ARRHYTHMIA TYPE

(75) Inventors: Jie Lian, Beaverton, OR (US); Volker Lang, West Linn, OR (US)

(73) Assignee: Biotronik SE & Co. KG (DE)

( * ) Notice: Subject to any disclaimer, the term of this patent is extended or adjusted under 35 U.S.C. 154(b) by 0 days.

(21) Appl. No.: 13/430,750

(22) Filed: Mar. 27, 2012

(65) Prior Publication Data
US 2012/0265087 A1 Oct. 18, 2012

Related U.S. Application Data

(60) Provisional application No. 61/474,755, filed on Apr. 13, 2011.

(51) Int. Cl.
*A61B 5/0452* (2006.01)
(52) U.S. Cl.
USPC .......................................................... 600/515
(58) Field of Classification Search
USPC .......................................................... 600/515
See application file for complete search history.

(56) References Cited

U.S. PATENT DOCUMENTS

| | | | |
|---|---|---|---|
| 6,968,226 B2 | 11/2005 | Mehra et al. | |
| 2002/0188327 A1 | 12/2002 | Struble | |
| 2003/0191404 A1 | 10/2003 | Klein | |
| 2004/0267321 A1* | 12/2004 | Boileau et al. | 607/3 |
| 2009/0282330 A1 | 11/2009 | Hines et al. | |
| 2010/0100143 A1 | 4/2010 | Nigam et al. | |

FOREIGN PATENT DOCUMENTS

EP 2 123 326 A1 11/2009

OTHER PUBLICATIONS

European Search Report, Application No. 12159234.9-2319, Jul. 11, 2012.

* cited by examiner

*Primary Examiner* — Eric D. Bertram
(74) *Attorney, Agent, or Firm* — Craig A. Fieschko, Esq.; DeWitt Ross & Stevens S.C.

(57) ABSTRACT

The type of arrhythmia in a patient's heart can be determined by monitoring the atrial and ventricular rate of the heart; detecting a pathological initial ventricular and/or atrial rate during a first time period; if a pathological initial rate is detected, then administering at least one antiarrhythmic cardioactive drug over a short second time period; detecting the heart's response to the administered drug(s), as by comparing the responsive ventricular and atrial rates with the initial ventricular and atrial rates, respectively, within a third time period; and determining the type of atrial or ventricular arrhythmia from the presence or absence of differences, and the type of differences, between the responsive atrial and ventricular rates compared with the initial atrial and ventricular rates. The invention further involves a related device which includes an implantable cardiac device (10) and a drug delivery device (20).

23 Claims, 2 Drawing Sheets

METHODS AND DEVICES FOR DETERMINATION OF HEART ARRHYTHMIA TYPE

CROSS-REFERENCE TO RELATED APPLICATIONS

This application claims priority under 35 USC §119(e) to U.S. Provisional Patent Application 61/474,755 filed Apr. 13, 2011, the entirety of which is incorporated by reference herein.

FIELD OF THE INVENTION

The invention relates to a method for determining a type of arrhythmia in a patient's heart, and a related device including an implantable cardiac device, for example a pacemaker, defibrillator or cardioverter.

BACKGROUND OF THE INVENTION

An arrhythmia is an abnormal heart rhythm. One example of an arrhythmia is a tachyarrythmia, wherein the heart beats at an abnormally fast rate. With atrial tachycardia, the atria of the heart beats abnormally fast; likewise, with ventricular tachycardia, the ventricles of the heart beat abnormally fast. Though often unpleasant for the patient, an atrial tachycardia is typically not fatal. However, some tachycardia, particularly ventricular tachycardia, can trigger ventricular fibrillation wherein the heart beats chaotically resulting in little or no net flow of blood from the heart to the brain and organs. Ventricular fibrillation, if not terminated, may be fatal. Hence, it is highly desirable to prevent or terminate arrhythmia, particularly ventricular tachycardia, with an appropriate therapy.

Implanted medical devices are sometimes used to detect and treat a patient's arrhythmia. As an example, an implanted medical device may include a defibrillator which applies electrical therapy to a patient's heart upon detecting an atrial fibrillation. Cardioverters or defibrillators discharge relatively high energetic electrical shocks across cardiac tissue to arrest life-threatening ventricular fibrillation detected by the implanted medical device. Defibrillation shocks, while highly effective at arresting the fibrillation, may cause considerable patient discomfort and should therefore only be applied if they are really necessary. Other therapy of tachycardia or fibrillation includes drug administration, wherein the drugs are often highly specific with regard to the type of tachycardia or fibrillation.

In order to apply the most appropriate therapy to the patient suffering an arrhythmia, it is necessary to know the particular type of an arrhythmia occurring with a patient. For example, if high ventricular rate is accompanied by high atrial rate, then a decision needs to be made to distinguish SVT (Supra Ventricular Tachycardia) from VT (Ventricular Tachycardia). Although other criteria—such as sudden onset, stability, AV consistency, QRS morphology, etc. of a cardiac signal—can be used to facilitate the classification, the sensitivity and specificity of these methods are not sufficiently high. Further, these methods require substantial time to make a distinction between different arrhythmia types.

It would therefore be useful to have methods and devices for reliably and quickly determining the type of arrhythmia, with high sensitivity and specificity, so that the most appropriate therapy might be provided to the patient shortly after detection of the arrhythmia.

US Patent Appl'n. Publ'n. 2004/0267321 A1 describes an implantable cardiac stimulation device which is configured to automatically monitor the effects of antiarrhythmic drugs on cardiac electrical signals within a patient to verify the efficacy of the drugs taken. The device utilizes atrial and ventricular sensing circuits to sense cardiac electric signals to determine whether a rhythm is physiologic or pathologic. The sensed signals are then processed in order to determine the presence of an arrhythmia. Timing intervals between sensed events (e.g., P-waves, R-waves, and depolarization signals associated with fibrillation, which are sometimes referred to as "F-waves" or "FIB-waves") are classified by a microcontroller by comparing them to a predefined rate zone limit and various other characteristics (e.g., sudden onset, stability, physiologic sensors, morphology, etc.). The device further includes an antiarrhythmic drug efficacy monitoring unit for automatically monitoring the efficacy of antiarrhythmic drugs prescribed to the patient. The monitoring unit therefore includes a cardiac signal analysis unit for analyzing the patient's cardiac signal to verify the efficacy of the prescribed drugs, and a warning signal generation unit for generating a warning signal alerting the patient or physician to possible drug efficacy problems. The monitoring unit also includes a drug pump control unit for automatically controlling an optional implantable drug pump to compensate, if necessary, for drug efficacy problems. For example, if an initial dosage of an antiarrhythmic drug is not adequately effective, the drug pump may be controlled to increase the dosage. Additionally, the device includes a monitoring unit including a control parameter adjustment unit for automatically adjusting pacing control parameters used by the implanted device to compensate for drug efficacy problems. For example, if the prescribed antiarrhythmic drug is not adequately effective, overdrive pacing control parameters can be adjusted to increase the aggressiveness of overdrive pacing.

A disadvantage of the device of US 2004/0267321 A1 is that it is slow to determine arrhythmia, and stabilization of antiarrhythmic drug delivery also takes time.

U.S. Pat. No. 6,968,226 B2 is directed to an implanted device which automatically prevents and/or terminates an atrial arrhythmia in a patient's heart using pacing and/or pharmaceutical therapies. The device measures at least one electrocardiogram characteristic indicative of an atrial arrhythmia, thereby detecting an atrial arrhythmia of the heart, and thereafter transmits a warning signal to the patient. Instead of, or in addition to, the traditional electrical cardioversion therapy, the patient chooses a pharmaceutical therapy via an available drug delivery arrangement, for example via an external drug delivery arrangement (e.g. intravenously, orally, transdermally, intramuscularly, orally, inhalationally, among others) to terminate the atrial fibrillation. While delivering the drug therapy or shortly thereafter, the implanted medical device measures at least one additional Q-T interval and denominates it as the drug therapy Q-T interval. Drug therapy is terminated if a drug therapy Q-T interval is measured to be greater than a drug therapy Q-T interval threshold. For example, drug therapy is stopped if the Q-T interval after initiation of drug therapy is measured to exceed 500 ms Like the system of the aforementioned 2004/0267321 A1, this system is also slow to determine arrhythmic type, and involves a long term therapy of arrhythmia as well.

SUMMARY OF THE INVENTION

The shortcomings of the prior systems can be at least partially addressed by a method for determining a type of an atrial or ventricular arrhythmia in a patient's heart, wherein the method includes the steps of:
monitoring the atrial and ventricular rate of the heart;

detecting a pathological initial ventricular and atrial rate during a first time period;

if a pathological initial ventricular and atrial rate is detected, then administering, preferably intravenously administering, at least one antiarrhythmic cardioactive drug over a second time period, preferably over a short time period of 1 to 10 seconds;

detecting the response of the ventricular and atrial rate of the heart to the administration of the drug(s), as by comparing the ventricular and atrial rate response with the initial ventricular and atrial rate, respectively, within a third time period and determining the existence and type of any differences therebetween; and determining the type of atrial or ventricular arrhythmia from the presence or absence of differences between the atrial and ventricular rate response compared with the initial atrial and ventricular rate, and from the type of these differences.

The invention also encompasses a system including an implantable cardiac device and a drug delivery device configured to implement the foregoing method. The method and system can instead be implemented to use just atrial rates or just ventricular rates, though use of both atrial and ventricular measurements is preferred.

The proposed method and device utilize the observation that certain drugs have highly effective influence on the ventricular or atrial rate, wherein such influence is specific with regard to a certain type of arrhythmia. Hence, it is possible to determine the type of atrial or ventricular arrhythmia quickly, and with high sensitivity and specificity. As a result, appropriate therapy can be initiated with improved efficacy.

The invention utilizes the concept that a highly efficient drug can be administered over a very short time (and in a small amount) merely to observe the response of the heart so that the type of arrhythmia can be determined. Using the proposed short diagnostic drug pulse, which is provided in a considerably smaller amount than a therapeutic dosage, the type of arrhythmia can be quickly determined, and any possibly negative effects on heart behavior or patient health can be minimized. Since the invention can allow correct and reliable determination of the type of arrhythmia, and thereby allow more rapid implementation of the most effective therapy for the patient, thereby offsetting any negative effects.

The antiarrhythmic cardioactive drug(s) are preferably administered intravenously, or directly into the heart. The drug(s) may be provided in the form of one or more medicaments, steroids, and/or monoclonal antibodies, any of which may be encapsulated (or unencapsulated), and/or which may contain additives, matrix substances, and/or which may include other components or features known in the field.

In a preferred version of the invention, the cardiac device includes a control unit which processes data; a detection unit for monitoring of the atrial and ventricular rate; a memory unit; and a power supply. The control unit controls the drug delivery device in order to administer the antiarrhythmic cardioactive drug(s), and processes data received from the detection unit, in particular the measured atrial and ventricular rate of the patient's heart. The drug delivery device preferably includes a pump and at least one drug reservoir. The cardiac device may further include electrodes for application of pacing or shock energy to the heart, and/or the drug delivery device may include further drug reservoirs in order to apply therapeutical drug doses.

In an exemplary version of the invention, the second time period for administering the antiarrhythmic cardioactive drug (s) takes 1 to 3 seconds, with the drug delivering device being adapted to administer the drug(s) during this proposed time interval. This time interval is usually sufficient for the proposed diagnostic utilization of the drug, evoking a response of the ventricular and atrial rate sufficient to determine the type of atrial and ventricular arrhythmia.

In another version the antiarrhythmic cardiactive drug(s) includes adenosine. Adenosine is a naturally occurring nucleoside that, when given intravenously, has a rapid peak effect (typically 10 to 30 seconds) manifested by transient high degree AV block and profound slowing of the AV node, or both. Moreover, it is removed from the circulation very quickly, and its half-life is less than 10 seconds. Furthermore, adenosine is usually well tolerated by the patients. These characteristics make adenosine highly effective for the determination of the type of atrial tachycardia, in particular for acute determination of the AV nodal dependent tachyarrhythmias. Furthermore, not only an AV nodal dependent tacharrhythmia can be determined but as a by-product of the diagnostic drug release, often AV nodal reentry and bypass-tract-mediated reentry arrhythmia can be terminated by an intravenous bolus of adenosine. Although adenosine may not terminate other types of SVT that do not depend on the AV node, such as atrial tachycardia, atrial fibrillation, and atrial flutter, the transient AV block caused by adenosine can transiently slow atrial tachyarrhythmias. For a ventricular tachycardia, however, adenosine typically has no effect. Accordingly, in one version an adenosine bolus is utilized to discriminate between AV nodal dependent SVT, SVT (not AV nodal dependent) and VT arrhythmia as described below.

As a result, many inappropriate therapies (antitachycardia pacing or shock) can be avoided. When a patient is experiencing SVT, inappropriate pacing/shock therapy to treat VT is ineffective, may cause patient discomfort or pain (inappropriate shock), and may actually induce VT. When a patient is experiencing VT, inappropriate pacing/shock therapy to treat SVT may be subject the patient to greater time without appropriate VT therapy. Moreover, the efficacy of current pacing therapy to treat SVT is very limited.

The inventive concept noted above need not be applied to detect all tachycardias, and additional methods may be used in conjunction with the invention. For example, if the ventricular rate is high, e.g., higher than 150 bpm (though any suitable value may be defined in advance, possibly on a patient-by patient basis) and higher than the atrial rate, VT might be diagnosed without using the invention, and appropriate ventricular therapy can be initiated.

In the case of high ventricular rate with an atrial rate greater than or equal to the ventricular rate during the first time period, the cardiac device can designate a pathological initial ventricular and atrial rate. In this situation the patient may be suffering a SVT rather than a VT, but VT cannot yet be excluded as from the diagnosis. To determine if the underlying arrhythmia is SVT or VT, the device can trigger a transient release of a diagnostic dose of the antiarrhythmic cardioactive drug during the second period of time, for example, administration of a bolus of adenosine of 6 mg for 1 to 2 seconds. Immediately thereafter, the detection unit of the cardiac device detects the response of the ventricular and atrial rate of the heart within a third time period. If the detection unit determines that both the atrial and ventricular rate response are slowed (e.g., to less than 150 bpm or some other pre-defined value) within the third time period, an AV nodal dependent SVT is determined by the cardiac device (e.g., within its control unit), such as AV nodal reentry or bypass-tract-mediated macro reentry. Typically the episode will be successfully terminated by the short adenosine pulse. Details of the event can be logged into a memory of the cardiac device. Stability criteria within the third time period, e.g., stability criteria as discussed in US 2010/0100143 A1 (which is incorporated herein by reference), may be used by the detection unit of the cardiac device in order to determine an AV nodal dependent SVT.

If only the ventricular rate response has changed (i.e. slowed to less than 150 bpm or some other predetermined value) within the third time period, whereas the atrial rate response has not changed in comparison compared with the initial ventricular rate and initial atrial rate, the control unit of the cardiac device can designate an SVT that is not dependent on the AV node, such as atrial tachycardia, atrial fibrillation, or atrial flutter.

If the detection unit determines that neither the ventricular rate nor the atrial rate has changed within the third time period, the control unit of the cardiac device can designate the existence of VT.

In each case, the control unit of the cardiac device can then initiate the appropriate therapy to the patient according to the determined type of arrhythmia, and/or the cardiac device can display or otherwise provide information regarding to the determined arrhythmia type (as by sending the information to an external unit). The determined arrhythmia type may also be stored within a memory of the cardiac device for later processing.

The third time period preferably begins immediately after the start of the second time period, preferably 1 to 3 seconds after the start of the second time period or directly after the end of the second time period. Such a real-time response is possible, for example, with adenosine, and is useful for quick diagnosis and action.

These and other advantages of features of the invention will become apparent to those of ordinary skill in the art after review of the following detailed description and the accompanying drawings.

BRIEF DESCRIPTION OF THE DRAWINGS

Exemplary versions of the invention are described below with reference to the accompanying drawings, wherein.

DETAILED DESCRIPTION OF PREFERRED VERSIONS OF THE INVENTION

Figure 1:
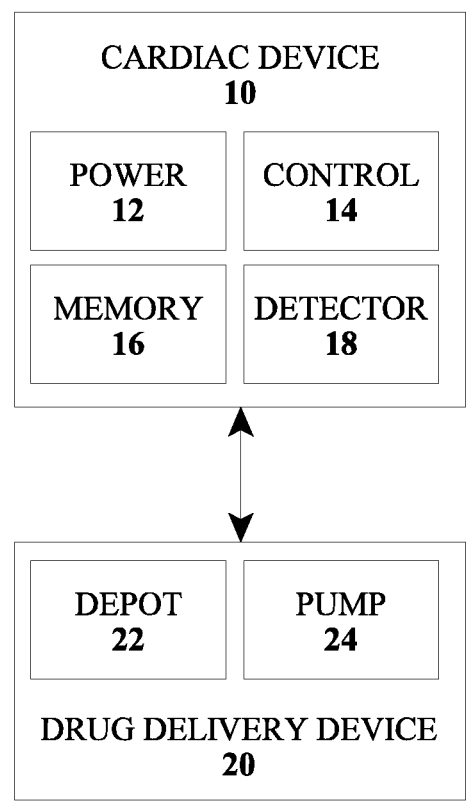
FIG. 1 schematically illustrates an exemplary version of a device according to the invention.

FIG. 1 shows an version of a device for determination of an atrial and ventricular arrhythmia in a patient's heart including an implantable cardiac device 10 (e.g., a pacemaker, defibrillator or cardioverter), and a drug delivery device 20, which may be implantable or an external device, and which preferably includes a drug depot/reservoir 22 and a pump or other supply mechanism 24. For example, the implantable cardiac device 10 and the drug delivery device 20 may form a combined system as described in EP 2 123 326 A1 and US 2009/0292330 A1, which are incorporated herein by reference. The connecting line between the cardiac device 10 and a drug delivery device 20 indicates a communications connection between the devices, which may be wired or wireless via appropriate interfaces.

The cardiac device 10 includes a power supply 12, a control unit 14, a memory 16 and a detection unit 18 which are connected with each other and are not shown in FIG. 1. The detection unit 18 is adapted to sense the atrial and the ventricular rate of the heart of the patient. The control unit 14 processes the signals sensed by the detection unit 18 and is adapted to control the additional functions of the cardiac device, for example the operation of a pacing or shock electrode (not shown), and the operation of the drug delivery device 20.

Figure 2:
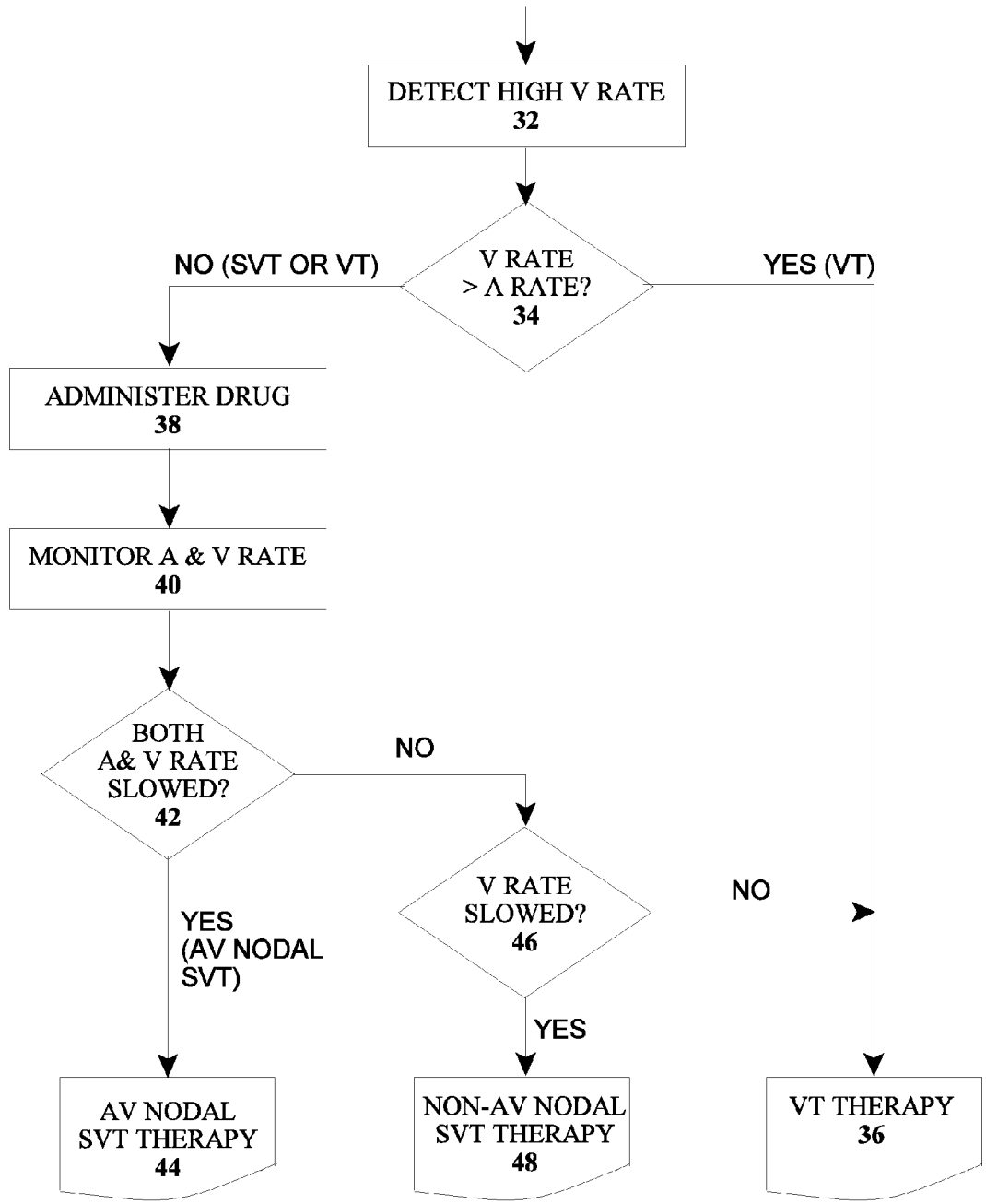
FIG. 2 shows a simplified flow chart of an exemplary version of an inventive method.

A preferred operational mode of the cardiac device 10 and the drug delivery device 20 of FIG. 1 is depicted in the flowchart of FIG. 2. Based on an examination of the atrial and ventricular response after intravenous release of adenosine, a fast diagnostic decision of SVT or VT can be made with high sensitivity and specificity using the depicted method.

At first, the detection unit of the cardiac device 10 detects a high ventricular rate in step 32, e.g., 150 bpm (beats per minute) or some other desired threshold. Then, the control unit 14 of the cardiac device 10 compares the ventricular rate with the atrial rate in step 34. If the ventricular rate is higher than the atrial rate the procedure continues with the YES branch of the flow diagram, and a VT is diagnosed in step 36 by the control unit 14 which then initiates an appropriate ventricular therapy (e.g., ventricular anti-tachycardia pacing, low energy cardioversion, and/or high energy shock, depending on the programmed tiered therapy settings). Alternatively, a trigger can be generated at the control unit 14 to cause the release of certain antiarrhythmic drugs, such as lidocaine, from the drug delivery device 20.

If the atrial rate is higher than or equal to the ventricular rate the procedure continues with step 38 and a decision needs to be made to distinguish SVT from VT arrhythmia. According to the invention, then, the control unit of the cardiac device 10 triggers the pump 24 of the drug delivery device 20 to administer an intravenous dose of adenosine (or other suitable drug) within a second time period. In a preferred implementation, a dose of 6 mg adenosine is released for one or two seconds.

Directly after administration of the adenosine bolus, i.e. for example 1-3 seconds after the start of the second time period or directly after the end of the second time period, the cardiac device 10 continues monitoring the atrial and ventricular rate over a third period of time in step 40, for example 3 to 4 seconds, or over a number of cardiac cycles (e.g. 8 to 10 cycles), with the third period preferably being user-programmable.

In step 42 the control unit 14 of the cardiac unit 10 decides whether both the atrial rate and the ventricular rate are slowed within the third time period after the adenosine release, e.g., whether the detected atrial rate and the detected ventricular rate each are below 150 bpm.

If both the atrial rate and the ventricular rate are slowed, the procedure continues with step 44, wherein a diagnosis of AV nodal dependent SVT is made, such as AV nodal reentry or bypass-tract-mediated macroreentry. In most cases, the short pulse of adenosine will successfully terminate the event, but additional or other therapy may be applied if needed. In any event, the event is preferably logged into the memory 16 of the cardiac device 10.

If one of the atrial rate and the ventricular rate is not slowed within third time period, the procedure continues with step 46. In this step the control unit 14 decides whether only the ventricular rate is slowed within third time period, e.g., if the ventricular rate drops below 150 bpm. If slowing of the ventricular rate occurred, step 48 delivers the diagnosis of SVT which is not dependent on the AV node (such as atrial tachycardia, atrial fibrillation or atrial flutter). Correspondingly, in step 48 an atrial therapy (e.g., atrial anti-tachycardia pacing or atrial cardioversion) is initiated in order to terminate the SVT. Alternatively, a trigger may be generated by the control unit 14 to cause intravenous release of certain antiarrhythmic drugs, such as verapamil, diltiazem procainamide, etc. by the pump 24 of the drug delivery device 20, in order to terminate the SVT or to slow the ventricular response.

If neither the atrial rate nor the ventricular rate or rhythm has changed after application of the adenosine bolus within the third time period, the "no" path from step 46 is followed, and the control unit 14 diagnoses VT arrhythmia at step 36, and an appropriate therapy is initiated to terminate the VT.

It will be apparent to those skilled in the art that numerous modifications and variations of the described examples and versions are possible in light of the foregoing discussion. The described examples and versions are presented for purposes of illustration only, and alternative versions may include some or all of the features disclosed herein. The invention is therefore not intended to be limited to the exemplary versions of the invention described above, but rather is intended to be limited only by the claims set out below. Thus, the invention encompasses all different versions that fall literally or equivalently within the scope of these claims.

What is claimed is:

1. A method performed in an implantable system for determining a type of an arrhythmia in a patient's heart, the method including the steps of:
    a. monitoring initial atrial and ventricular rates of the heart;
    b. detecting a pathological initial ventricular and/or atrial rate;
    c. upon detecting a pathological initial ventricular and/or atrial rate during a first time period:
        (1) administering a nontherapeutic amount of an antiarrhythmic cardioactive drug over a second time period, the nontherapeutic amount being less than a therapeutic amount typically prescribed for the pathological initial ventricular and/or atrial rate;
        (2) detecting the response of the ventricular and atrial rates to the nontherapeutic amount of the drug;
        (3) determining differences between:
            (a) the ventricular and atrial rates in response to the drug, and
            (b) the initial atrial and ventricular rates;
        (4) determining a type of atrial or ventricular arrhythmia from the differences.

2. The method of claim 1 wherein the second time period is less than 10 seconds.

3. The method of claim 1 wherein the second time period is 1 to 3 seconds.

4. The method of claim 1 wherein the antiarrhythmic cardioactive drug includes adenosine.

5. The method of claim 1 wherein the antiarrhythmic cardioactive drug is administered intravenously.

6. The method of claim 1 wherein a pathological initial ventricular and atrial rate is detected during the first time period if the atrial rate is greater than or equal to the ventricular rate during the first time period.

7. The method of claim 6 wherein if the ventricular rate has slowed in response to the drug but the atrial rate has not slowed in response to the drug, electrical stimulation is delivered to the heart.

8. The method of claim 1 wherein the differences between:
    a. the ventricular and atrial rates in response to the drug, and
    b. the initial atrial and ventricular rates, are determined over a third time period starting after the start of the second time period.

9. The method of claim 8 wherein the third time period starts after the end of the second time period.

10. The method of claim 8 wherein the third time period begins 1-3 seconds after the start of the second time period.

11. A method performed in an implantable system for determining a type of an arrhythmia in a patient's heart, the method including the steps of:
    a. monitoring initial atrial and ventricular rates of the heart;
    b. detecting a pathological initial ventricular and/or atrial rate wherein the atrial rate is greater than or equal to the ventricular rate;
    c. upon detecting a pathological initial ventricular and/or atrial rate during a first time period:
        (1) administering an antiarrhythmic cardioactive drug over a second time period;
        (2) detecting the response of the ventricular and atrial rates to the drug;
        (3) determining differences between:
            (a) the ventricular and atrial rates in response to the drug, and
            (b) the initial atrial and ventricular rates;
        (4) determining a type of atrial or ventricular arrhythmia from the differences, wherein if both the ventricular and atrial rates are slowed in response to the drug, an AV nodal dependent SVT is determined.

12. A method performed in an implantable system for determining a type of an arrhythmia in a patient's heart, the method including the steps of:
    a. monitoring initial atrial and ventricular rates of the heart;
    b. detecting a pathological initial ventricular and/or atrial rate wherein the atrial rate is greater than or equal to the ventricular rate;
    c. upon detecting a pathological initial ventricular and/or atrial rate during a first time period:
        (1) administering an antiarrhythmic cardioactive drug over a second time period;
        (2) detecting the response of the ventricular and atrial rates to the drug;
        (3) determining differences between:
            (a) the ventricular and atrial rates in response to the drug, and
            (b) the initial atrial and ventricular rates;
        (4) determining a type of atrial or ventricular arrhythmia from the differences, wherein if the ventricular rate has slowed in response to the drug but the atrial rate has not slowed in response to the drug, an SVT which is not dependent on the AV node is determined.

13. A method performed in an implantable system for determining a type of an arrhythmia in a patient's heart, the method including the steps of:
    a. measuring an initial atrial and ventricular rate of the heart over a first time period;
    b. monitoring the initial atrial and ventricular rate of the heart for:
        (1) a pathological initial ventricular rate, and/or
        (2) a pathological initial atrial rate,
    c. upon detection of a pathological initial rate:
        (1) administering a nontherapeutic amount of an antiarrhythmic cardioactive drug during a second time period, the nontherapeutic amount being less than a therapeutic amount typically prescribed for the pathological initial ventricular and/or atrial rate;
        (2) measuring the response of the atrial and ventricular rate of the heart to the nontherapeutic amount of the drug,
        (3) comparing the response of the atrial and ventricular rate of the heart to the initial atrial and ventricular rate over a third time period;

(4) determining the type of atrial or ventricular arrhythmia from any differences between the response of the atrial and ventricular rate of the heart and the initial atrial and ventricular rate.

14. The method of claim 13 wherein the atrial or ventricular arrhythmia is determined to be an AV nodal dependent SVT if both the ventricular and atrial rates are slowed in response to the drug.

15. The method of claim 13 wherein the atrial or ventricular arrhythmia is determined to be an SVT which is not dependent on the AV node if the ventricular rate has slowed in response to the drug but the atrial rate has not slowed in response to the drug.

16. The method of claim 13 wherein the second time period is 1 to 3 seconds.

17. An implantable device for determining a type of an arrhythmia in a patient's heart, the device being configured to:
   a. monitor initial atrial and ventricular rates of the heart;
   b. detect a pathological initial ventricular and/or atrial rate;
   c. administer a nontherapeutic amount of an antiarrhythmic cardioactive drug over a second time period upon detection of a pathological initial ventricular and/or atrial rate during a first time period, the nontherapeutic amount being less than a therapeutic amount typically prescribed for the pathological initial ventricular and/or atrial rate;
   d. detect the response of the ventricular and atrial rates to the drug;
   e. determine a type of atrial or ventricular arrhythmia from any differences between:
      (1) the ventricular and atrial rates in response to the drug, and
      (2) the initial atrial and ventricular rates.

18. The device of claim 17 wherein the device includes a drug reservoir containing adenosine.

19. The device of claim 17 wherein the device includes a pump in communication with a drug reservoir.

20. The device of claim 17 wherein the drug delivering device is configured to administer the antiarrhythmic cardioactive drug for 1 to 3 seconds during the second time period.

21. The device of claim 17 wherein the device is configured to detect a pathological initial ventricular and/or atrial rate during the first time period if the atrial rate is greater than or equal to the ventricular rate during the first time period.

22. An implantable device for determining a type of an arrhythmia in a patient's heart, the device being configured to:
   a. monitor initial atrial and ventricular rates of the heart;
   b. detect a pathological initial ventricular and/or atrial rate;
   c. administer an antiarrhythmic cardioactive drug over a second time period upon detection of a pathological initial ventricular and/or atrial rate during a first time period;
   d. detect the response of the ventricular and atrial rates to the drug;
   e. determine a type of atrial or ventricular arrhythmia from any differences between:
      (1) the ventricular and atrial rates in response to the drug, and
      (2) the initial atrial and ventricular rates,
   wherein an AV nodal dependent SVT is determined if both the ventricular and atrial rates are slowed in response to the drug.

23. An implantable device for determining a type of an arrhythmia in a patient's heart, the device being configured to:
   a. monitor initial atrial and ventricular rates of the heart;
   b. detect a pathological initial ventricular and/or atrial rate;
   c. administer an antiarrhythmic cardioactive drug over a second time period upon detection of a pathological initial ventricular and/or atrial rate during a first time period;
   d. detect the response of the ventricular and atrial rates to the drug;
   e. determine a type of atrial or ventricular arrhythmia from any differences between:
      (1) the ventricular and atrial rates in response to the drug, and
      (2) the initial atrial and ventricular rates,
   wherein an SVT which is not dependent on the AV node is determined if the ventricular rate has slowed in response to the drug but the atrial rate has not slowed in response to the drug.

* * * * *